United States Patent [19]
Kelly et al.

[11] Patent Number: 6,066,637
[45] Date of Patent: May 23, 2000

[54] INDOLYL DERIVATIVES AS SEROTONERGIC AGENTS

[75] Inventors: Michael G. Kelly, Plainsboro; Young H. Kang, Robbinsville, both of N.J.

[73] Assignee: American Home Products Corporation, Madison, N.J.

[21] Appl. No.: 09/298,202

[22] Filed: Apr. 23, 1999

Related U.S. Application Data

[60] Provisional application No. 60/100,433, Apr. 29, 1998.

[51] Int. Cl.$^7$ ...................... A61K 31/495; A61K 31/445; C07D 401/14
[52] U.S. Cl. .......................... 514/253; 514/316; 514/318; 544/295; 544/333; 544/364; 546/187; 546/193; 546/194
[58] Field of Search ..................................... 544/364, 295, 544/333; 546/187, 193, 194; 514/253, 316, 318

[56] References Cited

U.S. PATENT DOCUMENTS

| | | | |
|---|---|---|---|
| 5,342,845 | 8/1994 | Chokai et al. | 514/305 |
| 5,565,447 | 10/1996 | Forner et al. | 514/212 |
| 5,607,960 | 3/1997 | Wythes | 514/414 |
| 5,607,961 | 3/1997 | Cipollina et al. | 514/415 |
| 5,614,523 | 3/1997 | Audia et al. | 514/252 |
| 5,639,752 | 6/1997 | Macor | 514/245 |
| 5,639,772 | 6/1997 | Hammarberg et al. | 514/374 |
| 5,641,794 | 6/1997 | Booher et al. | 514/364 |
| 5,654,320 | 8/1997 | Catlow et al. | 514/322 |
| 5,654,324 | 8/1997 | Booher et al. | 514/387 |
| 5,670,511 | 9/1997 | Marz et al. | 514/290 |
| 5,693,655 | 12/1997 | Bottcher et al. | 514/323 |
| 5,708,008 | 1/1998 | Audia et al. | 514/323 |
| 5,792,763 | 8/1998 | Fritz et al. | 514/228.2 |

FOREIGN PATENT DOCUMENTS

99/20621   4/1999   WIPO.

OTHER PUBLICATIONS

Walker et al., Chemical Abstracts, vol. 130, No. 311818, (Abstract for WO 9920621, Apr. 29, 1999).
Gueremy et al., J. Med. Chem., 1980, 23, 1306–1310.
Malleron et al., J. Med. Chem., 1993, 36, 1194–1202.
Bergman, J. Heterocyclic Chem., 1970, 1071–1076.
Guillaume et al., Eur. J. Med. Chem., 1987, 22(1), 33–34.
Cheetham et al., Neuropharmacol. 32: 737, 1993.
Cheng and Prusoff, Biochem. Pharmacol., 22, 3099, 1973.
Bowen et al., TINS, vol. 17, No. 4, 1994.
Freter et al., Arzneim.–Forsch. 35 (1), 272–276, 1985.

*Primary Examiner*—Emily Bernhardt
*Attorney, Agent, or Firm*—Steven R. Eck

[57] ABSTRACT

The present invention provides compounds represented by the general formula (1)

(1)

wherein
  $R_1$ is selected from H, OH, $OR_2$ or halogen (F, Cl, Br, I);
  $R_2$ is lower alkyl ($C_1$ to $C_6$);
  n is selected from 0, 1 or 2;
  X is CH or $CH_2$;
  m is selected from 2, 3 or 4;
  Y is N or $CH_2$;
  Ar is aryl or heteroaryl, both optionally substituted;
or pharmaceutically acceptable salts thereof, as well as methods and pharmaceutical compositions utilizing these compounds for the inhibition of serotonin uptake and the treatment of CNS disorders, particularly depression.

11 Claims, No Drawings

INDOLYL DERIVATIVES AS SEROTONERGIC AGENTS

This application claims the benefit of U.S. Provisional Application No. 60/100,433, which was converted from U.S. patent application Ser. No. 09/069,043, filed Apr. 29, 1998, pursuant to a petition filed under 37 C.F.R. 1.53(c)(2)(i).

This invention relates to novel compounds useful as serotonergic agents. More particularly, this invention concerns indolyl compounds which are useful as serotonergic agents, particularly as serotonin re-uptake inhibitors.

BACKGROUND TO THE INVENTION

Depression is a psychiatric condition thought to be associated with decreased serotonin release. Most antidepressant agents potentiate the effects of serotonin by blocking the termination of its activity through re-uptake into nerve terminals.

U.S. Pat. No. 5,342,845 (Chokai et al.) teaches indole carboxamide derivatives of the general formula:

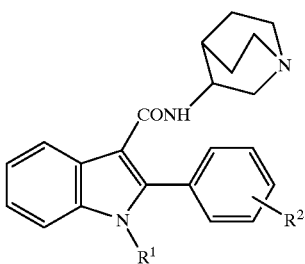

wherein $R^1$ is lower alkyl and $R^2$ is selected from H, halogen, lower alkyl or lower alkoxy, useful for gastrointestinal motor activity regulation, antimigraine, antipsychotic or antianxiety drugs.

U.S. Pat. No. 5,614,523 (Audia et al.) teaches hetero-oxy alkanamines which are effective in treatments for conditions related to or affected by the reuptake of serotonin and by the serotonin $1_A$ receptor.

U.S. Pat. No. 5,693,655 (Bottcher et al.) discloses 3-indolylpeperidines which exhibit action on the central nervous system, particularly dopamine-agonistic or dopamine-antagonistic actions.

U.S. Pat. No. 5,670,511 (Marz et al.) claims indolepiperidine derivatives also having dopamine agonistic or antagonistic action, the compounds having the general formula below, wherein $R^2$ is selected from —NH—CO—Ar, —NH—SO$_2$—Ar, or D, wherein D is as also shown below:

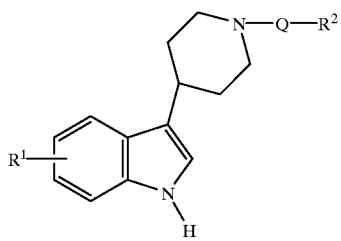

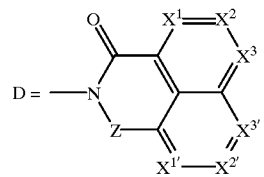

U.S. Pat. Nos. 5,541,794 and 5,654,324 (both to Booher et al.) claim 6-heterocyclic-4-amino-1,2,2a,3,4,5-hexahydrobenz-[cd] indoles useful in modifying the function of serotonin in mammals.

U.S. Pat. No. 5,654,320 (Catlow et al.) also disclose indazolecarboxamides useful as antagonists and partial agonists for the serotonin 5-HT$_4$ receptor and treatments for dysfunctions thereof.

This invention relates to novel indolyl derivatives, to processes for their preparation, to pharmaceutical compositions containing them and to their use in therapy. The novel compounds are useful for the treatment of central nervous system disorders, particularly depression, by virtue of their ability to inhibit the uptake of serotonin.

SUMMARY OF THE PRESENT INVENTION

Compounds of the present invention are represented by the general formula (1)

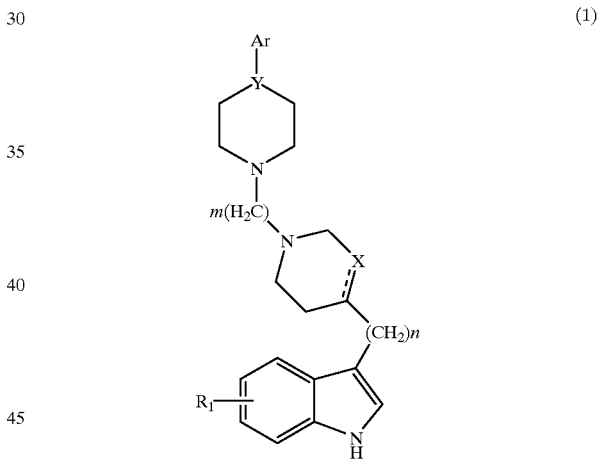

(1)

wherein:
$R_1$ is selected from H, OH, OR$_2$, F, Cl, Br, or I;
$R_2$ is lower alkyl (C$_1$ to C$_6$);
n is selected from 0, 1 or 2;
X is CH or CH$_2$;
m is an integer selected from 2, 3 or 4;
Y is N or CH$_2$;
Ar is aryl or heteroaryl, both optionally substituted by from one to three groups selected from F, Cl, Br, I, —OH, —CN, lower alkoxy (C$_1$ to C$_6$) or lower alkyl (C$_1$ to C$_6$); or a pharmaceutically acceptable salt thereof.

A preferred subset of compounds of this invention are those in which Y is nitrogen and $R_1$, $R_2$, n, X, m, Y and Ar are as defined above.

The preferred aryl or heteroaryl groups comprising Ar in the groups above are phenyl, benzodioxane, indole bonded to the Y moiety in the indole 4- or 7-position, pyridine, 2-pyrimidine, thiophene, furan or pyrrole. The most preferred of these groups are phenyl, benzodioxole-5-yl, and 2-pyrimidine.

The pharmaceutically acceptable salts are the acid addition salts which can be formed from a compound of the above general formula and a pharmaceutically acceptable inorganic acid, such as phosphoric, sulfuric, hydrochloric, hydrobromic, citric, maleic, furmaric, acetic, lactic or methanesulfonic acid.

DETAILED DESCRIPTION OF THE INVENTION

Compounds of the present invention may be prepared using conventional methods. For example, the appropriately substituted indole (A) can be coupled with a chloroalkyl-substituted arylpiperazine or arylpiperidine (B) using a base such as diisopropylethylamine. The product can then be used to form a pharmaceutically acceptable salt.

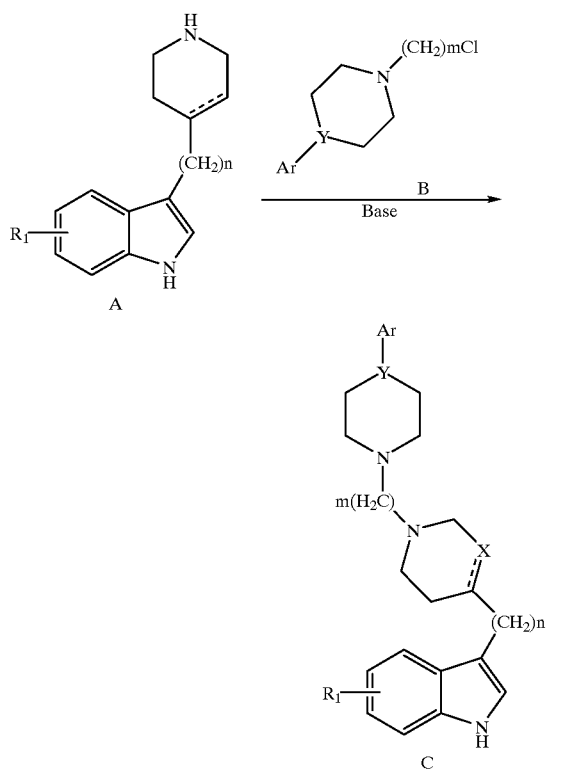

The preparation of the appropiately substituted 3-(4-piperidinyl)indoles and 3-(4-tetrahydro pyridinyl) indoles can be acheived by known and conventional methods. For example, the reaction of an optionally substituted indole (D) with 4-piperidone (E) affords the 3-(4-tetrahydropyridinyl) indole (F). This can be reduced using standard catalytic hydrogenation methodology to afford a 3-(4-piperidinyl) indole (G).

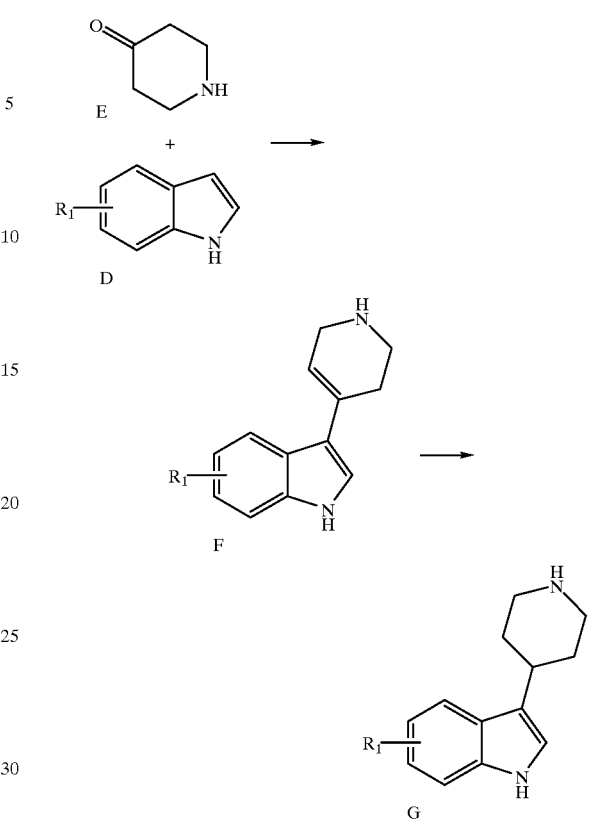

The preparation of the appropiately substituted 3-(4-piperidinylmethyl)indoles (H) and 3-(4-tetrahydropyridinylmethyl)indoles (I) can also be achieved by known and conventional methods. Such methodology is described in C. Gueremy et al., J. Med. Chem., 1980, 23, 1306–1310, J-L. Malleron et al., J. Med. Chem., 1993, 36, 1194–1202 and J. Bergman, J. Heterocyclic. Chem., 1970, 1071–1076.

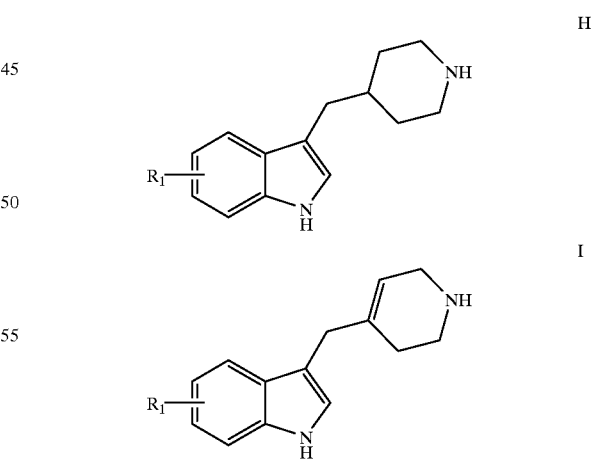

Compounds of the present invention inhibit with very high affinity the binding of paroxetine to the serotonin transporter and, consequently, are useful as antidepressant and anxiolytic agents for the treatment of central nervous system disorders such as depression, anxiety, sleep disorders, sexual dysfunction, alcohol and cocaine addiction, cognition enhancement and related problems. In addition, compounds of the present invention may be used in conjunction with an agonist or antagonist of the serotonin-1 receptor (5-HT1) to aid or enhance the compounds biological properties. Such compositions may be useful for the above mentioned disorders in addition to the treatment of Alzheimer's disease, Parkinson's disease, schizophrenia, obesity and migraine.

It is understood that the therapeutically effective dosage to be used in the treatment of a specific psychosis must be subjectively determined by the attending physician. Variables involved include the specific psychosis or state of anxiety and the size, age and response pattern of the patient. The novel method of the invention for treating conditions related to or are affected by the reuptake of serotonin comprise administering to warm-blooded animals, including humans, an effective amount of at least one compound of this invention or a non-toxic, pharmaceutically acceptable addition salt thereof. The compounds may be administered orally, rectally, parenterally, or topically to the skin and mucosa. The usual daily dose is depending on the specific compound, method of treatment and condition treated. An effective dose of 0.01–1000 mg/Kg may be used for oral application, preferably 0.5–500 mg/Kg, and an effective amount of 0.1–100 mg/Kg may be used for parenteral application, preferably 0.5–50 mg/Kg.

The present invention also includes pharmaceutical compositions containing a compound of this invention, or a pharmaceutically acceptable salt thereof, and one or more pharmaceutically acceptable carriers or excipients.

Applicable solid carriers or excipients can include one or more substances which may also act as flavoring agents, lubricants, solubilizers, suspending agents, fillers, glidants, compression aids, binders or tablet-disintergrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The affinity of drugs for the serotonin transporter was determined by assessing the ability of agents to displace specifically bound 3H-paroxetine binding from rat cortical membranes. A protocol similar to that used by Cheetham et al. (Neuropharmacol. 32:737, 1993) was used to determine the affinity of compounds for the serotonin transporter. Briefly, frontal cortical membranes prepared from male S.D. rats were incubated with $^3$H-paroxetine (0.1 nM) for 60 min at 25° C. All tubes also contained either vehicle, test compound (one to eight concentrations), or a saturating concentration of fluoxetine (10 μM) to define specific binding. All reactions are terminated by the addition of ice cold Tris buffer followed by rapid filtration using a Tom Tech filtration device to separate bound from free $^3$H-paroxetine. Bound radioactivity was quantitated using a Wallac 1205 Beta Plate® counter. Nonlinear regression analysis was used to determine $IC_{50}$ values which were converted to Ki values using the method of Cheng and Prusoff (Biochem. Pharmacol. 22: 3099, 1973);
Ki=IC50/((Radioligand conc.)/(1+KD)). Nonspecific binding was determined using fluoxetine. Using this assay, the following Ki's were determined for a series of standard serotonin uptake inhibitors.

| Compound | Inhibition of [3H]-Paroxetine binding Ki (nM) |
| --- | --- |
| Clomipramine | 0.18 |
| Fluoxetine | 4.42 |
| Imipramine | 17.6 |
| Zimelidine | 76.7 |

The results for a number of examples of compounds of formula 1 in this standard experimental test procedure were as follows:

| Compound | Inhibition of [3H]-Paroxetine binding Ki (nM) |
| --- | --- |
| Example 1 | 4.8 |
| Example 3 | 1.2 |
| Example 6 | 10.0 |
| Example 7 | 19.0 |

The following non-limiting specific examples are included to illustrate the synthetic procedures which may be used for preparing compounds of the formula 1. In these examples, all chemicals and intermediates are either commercially available or can be prepared by standard procedures found in the literature or are known to those skilled in the art of organic synthesis.

EXAMPLE 1

5-Fluoro-3-(1-{2-[4-(2-methoxyphenyl)piperazin-1-yl]ethyl}piperidin-4-ylmethyl)-1H-indole Pulverized potassium carbonate (0.76 g, 5.5 mmole) and potassium iodide (0.97 g, 5.5 mmole) was added to a mixture of 4-(5-fluoro-1H-indol-3-ylmethyl)piperidine (1.16 g, 5.0 mmole) and 1-(2-chloroethyl)-4-(2-methoxyphenyl)piperazine (1.27 g, 5.0 mmole) in 25 ml of acetonitrile. The resulting mixture was heated to reflux under nitrogen for 5 hours. After cooling, it was diluted with water (150 ml) and the product extracted into ethyl acetate (50 ml). The organic layer was washed with water (50 ml), brine (50 ml), and after drying over sodium sulfate, filtration and concentration in vacuo afforded the required product as a white solid (1.8 g, 80%). Treatment with an excess of 1M etheral hydrochloric acid gave the acid addition salt, which was recrystallized from methanol.

m.p. 253–254° C.; Elemental Analysis for: C27H35FN4O. 2HCl; Calculated: C, 61.95; H, 7.13; N, 10.68; Found: C, 61.84; H, 7.18; N, 10.61.

EXAMPLE 2

5-Fluoro-3-(1-{2-[4-(2-methoxyphenyl)piperazin-1-yl]ethyl}piperidin-4-yl)-1H-indole Pulverized potassium carbonate (0.35 g, 2.5 mmole) and potassium iodide (0.44 g, 2.5 mmole) was added to a mixture of 4-(5-fluoro-1H-indol-3-yl)piperidine (0.5 g, 2.3 mmole) and 1-(2-chloroethyl)-4-(2-methoxyphenyl)piperazine (0.58 g, 2.3 mmole) in 20 ml of acetonitrile. The resulting mixture was heated to reflux under nitrogen for 3 hours. After cooling, it was diluted with water (150 ml) and the product extracted into ethyl acetate (50 ml). The organic layer was washed with water (50 ml), brine (50 ml), and after drying over sodium sulfate, filtration and concentration in vacuo afforded the required product as a white solid (0.83 g, 83 %). Treatment with an excess of 1M etheral hydrochloric acid gave the acid addition salt, which was recrystallized from methanol.

m.p. 251–252° C.; Elemental Analysis for: C26H33FN4O. 2HCl. 0.25H2O; Calculated: C, 60.76; H, 6.96; N, 10.90; Found: C, 60.79; H, 7.09; N, 10.85.

EXAMPLE 3

5-Fluoro-3-(1-{3-[4-(2-methoxyphenyl)piperazin-1-yl]propyl}piperidin-4-ylmethyl)-1H-indole Pulverized potassium carbonate (0.33 g, 2.4 mmole) and potassium iodide (0.40 g, 2.4 mmole) was added to a mixture of 4-(5-fluoro-1H-indol-3-yl)methylpiperidine (0.5 g, 2.3 mmole) and 1-(2-chloroethyl)-4-(2-methoxyphenyl)piperazine (0.58 g, 2.3 mmole) in 20 ml of acetonitrile. The resulting mixture was heated to reflux under nitrogen for 3 hours. After cooling, it was diluted with water (150 ml) and the product extracted into ethyl acetate (50 ml). The organic layer was washed with water (50 ml), brine (50 ml), and after drying over sodium sulfate, filtration and concentration in vacuo afforded the required product as a white solid (0.78 g, 76%). Treatment with an excess of 0.25M ethanolic fumaric acid solution gave the acid addition salt, which was recrystallized from ethanol/diethyl ether to afford the title product as white needles.

m.p. 156–157° C.; Elemental Analysis for: C28H37FN4O. 2C4H4O4; Calculated: C, 62.06; H, 6.51; N, 8.04; Found: C, 61.76; H, 6.68; N, 7.87.

EXAMPLE 4

5-Fluoro-3-(1-{3-[4-(2-methoxyphenyl)piperazin-1-yl]propyl}piperidin-4-yl)-1H-indole The title compound was prepared using the procedure outlined in examples 1–3 above. The product was purified by silica gel column chromatography, and was isolated in 68% yield. Its fumaric acid salt was obtained as a fine white powder.

m.p. 200° C.; Elemental Analysis for: C27H35FN4O. 2C4H4O4; Calculated: C, 61.57; H, 6.35; N, 8.21; Found: C, 61.59; H, 6.53; N, 8.12.

EXAMPLE 5

3-(1-{2-[4-(2-methoxyphenyl)piperazin-1-yl]ethyl}piperidin-4-yl)-1H-indole

The title compound was prepared using the procedure outlined in examples 1–3 above. The product was purified by silica gel column chromatography, and was isolated in 96% yield as a white solid. Its fumaric acid salt was prepared as reported in example 3 and was obtained as a fine white powder.

m.p. 212–213° C.; Elemental Analysis for: C26H34N4O. 2C4H4O4; Calculated: C, 62.76; H, 6.51; N, 8.61; Found: C, 62.82; H, 6.48; N, 8.63.

EXAMPLE 6

3-(1-{2-[4-(2-methoxyphenyl)piperazin-1-yl]ethyl}1,2,3,6-tetrahydropyridin-4-yl)-1H-indole The title compound was prepared using the procedure outlined in examples 1–3 above. The product was purified by silica gel column chromatography, and was isolated in 64% yield as a light yellow solid. Its fumaric acid salt was prepared as reported in example 3.

m.p. 189° C.; Elemental Analysis for: C26H32N4O. 0.5C4H4O4; Calculated: C, 70.82; H, 7.26; N, 11.73; Found: C, 70.50; H, 7.27; N, 11.68.

EXAMPLE 7

5-Fluoro-3-(1-{2-[4-(2-methoxyphenyl)piperazin-1-yl]ethyl}1,2,3,6-tetrahydropyridin-4-yl)-1H-indole The title compound was prepared using the procedure outlined in examples 1–3 above. The product was purified by silica gel column chromatography, and was isolated in 69% yield as a yellow solid. Its fumaric acid salt was prepared as reported in example 3 and was obtained as a fine white solid.

m.p. 198–199° C.; Elemental Analysis for: C26H31FN4O. 2C4H4O4; Calculated: C, 61.25; H, 5.90; N, 8.40; Found: C, 61.37; H, 5.87; N, 8.46.

EXAMPLE 8

5-Fluoro-3-(1-{3-[4-(2-methoxyphenyl)1,2,3,6-tetrahydropyridin-1-yl]propyl}piperidin-4-ylmethyl)-1H-indole The title compound is prepared using the procedure outlined in examples 1–3 above. The product can be purified by silica gel column. Its fumaric acid salt may be prepared as reported in example 3.

EXAMPLE 9

5-Fluoro-3-(1-{2-[4-(2-fluorophenyl)piperazin-1-yl]ethyl}1,2,3,6-tetrahydropyridin-4-yl)-1H-indole The title compound is prepared using the procedure outlined in examples 1–3 above. The product may be purified by silica gel column. Its fumaric acid salt can be prepared as reported in example 3.

EXAMPLE 10

5-Fluoro-3-(1-{2-[4-(indol-4-yl)piperazin-1-yl]ethyl}1,2,3,6-tetrahydropyridin-4-yl)-1H-indole The title compound is prepared using the procedure outlined in examples 1–3 above. The product may be purified by silica gel column chromatography its fumaric acid salt prepared as reported in example 3.

What is claimed:

1. A compound according to Formula 1:

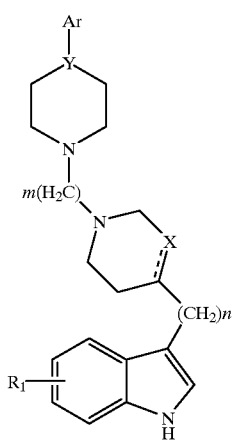

(1)

wherein;

$R_1$ is selected from H, OH, $OR_2$ F, Cl, Br, or I;

$R_2$ is lower alkyl ($C_1$ to $C_6$);

n is selected from 1 or 2;

X is CH or $CH_2$;

m is selected from 2, 3 or 4;

Y is N or $CH_2$;

Ar is phenyl, benzodioxane, indole bonded to the Y moiety in the indole 4- or 7-position, pyridine, 2-pyrimidine, thiophene, furan or pyrrole, each optionally substituted by from one to three groups selected from F, Cl, Br, I, —OH, —CN, lower alkoxy ($C_1$ to $C_6$) or lower alkyl ($C_1$ to $C_6$); or a pharmaceutically acceptable salt thereof.

2. A compound of claim 1 which is 5-Fluoro-3-(1-{2-[4-(2-methoxyphenyl)piperazin-1-yl]ethyl}piperidin-4-ylmethyl)-1H-indole or a pharmaceutically acceptable salt thereof.

3. A compound of which is 5-Fluoro-3-(1-{2-[4-(2-ethoxyphenyl)piperazin-1-yl]ethyl}piperidin-4-yl)-1H-indole or a pharmaceutically acceptable salt thereof.

4. A compound of claim 1 which is 5-Fluoro-3-(1-{3-[4-(2-methoxyphenyl)piperazin-1-yl]propyl}piperidin-4-ylmethyl)-1H-indole or a pharmaceutically acceptable salt thereof.

5. A compound of claim 1 which is 5-Fluoro-3-(1-{3-[4-(2-ethoxyphenyl)piperazin-1-yl]propyl}piperidin-4-ylmethyl)-1H-indole or a pharmaceutically acceptable salt thereof.

6. A compound which is 3-(1-{2-[4-(2-methoxyphenyl)piperazin-1-yl]ethyl}piperidin-4-yl)-1H-indole or a pharmaceutically acceptable salt thereof.

7. A compound which is 3-(1-{2-[4-(2-methoxyphenyl)piperazin-1-yl]ethyl}1,2,3,6-tetrahydropyridin-4-yl)-1H-indole or a pharmaceutically acceptable salt thereof.

8. A compound which is 5-Fluoro-3-(1-{2-[4-(2-methoxyphenyl)piperazin-1-yl]ethyl}1,2,3,6-tetrahydropyridin-4-yl)-1H-indole or a pharmaceutically acceptable salt thereof.

9. A pharmaceutical composition comprising a pharmaceutically acceptable carrier or excipient and a compound of claim 1, or a pharmaceutically acceptable salt thereof.

10. A method for treating depression in a mammal, the method comprising administering to a mammal in need thereof a therapeutically effective amount of a compound of claim 1, or a pharmaceutically acceptable salt thereof.

11. A method for treating anxiety in a mammal, the method comprising administering to a mammal in need thereof a therapeutically effective amount of a compound of claim 1, or a pharmaceutically acceptable salt thereof.

* * * * *